US008519097B2

(12) United States Patent
Heemskerk et al.

(10) Patent No.: US 8,519,097 B2
(45) Date of Patent: Aug. 27, 2013

(54) MOLECULES FOR TARGETING COMPOUNDS TO VARIOUS SELECTED ORGANS OR TISSUES

(75) Inventors: Johannes Antonius Heemskerk, Leiden (NL); Judith Christina Theodora Van Deutekom, Dordrecht (NL); Petra Van Kuik-Romeijn, Utrecht (NL); Gerard Johannes Platenburg, Voorschoten (NL)

(73) Assignee: Prosena Technologies B.V., Leiden (NL)

( * ) Notice: Subject to any disclaimer, the term of this patent is extended or adjusted under 35 U.S.C. 154(b) by 0 days.

(21) Appl. No.: 13/568,866

(22) Filed: Aug. 7, 2012

(65) Prior Publication Data
US 2012/0322724 A1 Dec. 20, 2012

Related U.S. Application Data

(60) Division of application No. 12/685,369, filed on Jan. 11, 2010, now Pat. No. 8,268,962, which is a continuation of application No. PCT/NL2008/050475, filed on Jul. 14, 2008.

(30) Foreign Application Priority Data

Jul. 12, 2007 (EP) .................................... 07112323

(51) Int. Cl.
*C07K 17/02* (2006.01)
(52) U.S. Cl.
USPC ........................................ 530/329; 435/69.7

(58) Field of Classification Search
None
See application file for complete search history.

(56) References Cited

U.S. PATENT DOCUMENTS

2007/0141628 A1    6/2007   Cunningham et al.

FOREIGN PATENT DOCUMENTS

| WO | WO-9853804 A1 | 12/1998 |
| WO | WO-03037172 A2 | 5/2003 |
| WO | WO-2004037854 A1 | 5/2004 |
| WO | WO-2005023836 A2 | 3/2005 |

OTHER PUBLICATIONS

Arap, W. et al. "Steps toward mapping the human vasculature by phage display", Nature Medicine, vol. 8, No. 2, Feb. 2002.
Samoylova, T. et al. "Elucidation of Muscle-Binding Peptides by Phage Display Screening", Muscle & Nerve, Apr. 1999, pp. 460-466.

*Primary Examiner* — John Ulm
(74) *Attorney, Agent, or Firm* — Sunstein Kann Murphy & Timbers LLP

(57) ABSTRACT

The invention provides conjugates, comprising an organ, tissue or tumor cell homing molecule linked to a moiety. Such a moiety can be, for example, an oligonucleotide, small interfering RNA, gene, virus, protein, pharmaceutical or detectable agent. In addition the invention provides methods to diagnose or treat a pathology of the muscle or heart, by administrating to a subject having or suspected of having a pathology a molecule or conjugate that homes to, binds to and is taken up by the muscle cells or heart cells.

10 Claims, 1 Drawing Sheet

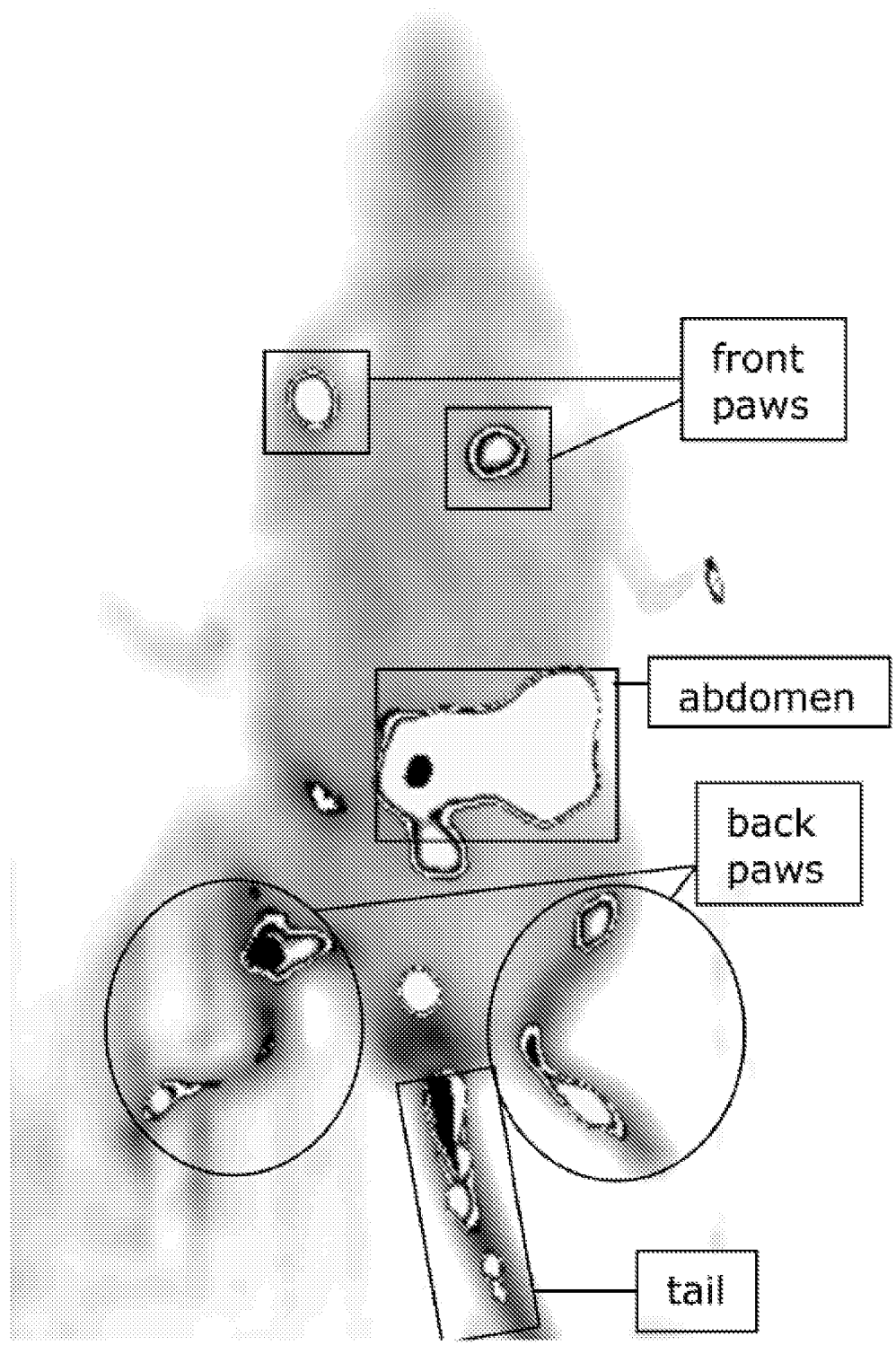

```
                        SEQUENCE LISTING

<160> NUMBER OF SEQ ID NOS: 115

<210> SEQ ID NO 1
   <211> LENGTH: 7
   <212> TYPE: PRT
   <213> ORGANISM: Artificial
   <220> FEATURE:
   <223> OTHER INFORMATION: Synthetic

<400> SEQUENCE: 1

Ser Pro Asn Ser Ile Gly Thr
   1               5

<210> SEQ ID NO 2
   <211> LENGTH: 7
   <212> TYPE: PRT
   <213> ORGANISM: Artificial
   <220> FEATURE:
   <223> OTHER INFORMATION: Synthetic

<400> SEQUENCE: 2

Ser Thr Phe Thr His Pro Arg
   1               5

<210> SEQ ID NO 3
   <211> LENGTH: 7
   <212> TYPE: PRT
   <213> ORGANISM: Artificial
   <220> FEATURE:
   <223> OTHER INFORMATION: Synthetic

<400> SEQUENCE: 3

Gln Leu Phe Thr Ser Ala Ser
   1               5

<210> SEQ ID NO 4
   <211> LENGTH: 7
   <212> TYPE: PRT
   <213> ORGANISM: Artificial
   <220> FEATURE:
   <223> OTHER INFORMATION: Synthetic

<400> SEQUENCE: 4

Ser Thr Ile His Gly Ser Thr
   1               5

<210> SEQ ID NO 5
   <211> LENGTH: 7
   <212> TYPE: PRT
   <213> ORGANISM: Artificial
   <220> FEATURE:
```

```
<223> OTHER INFORMATION: Synthetic

<400> SEQUENCE: 5

Ser Ala Pro Arg Pro Leu Tyr
1               5

<210> SEQ ID NO 6
<211> LENGTH: 7
<212> TYPE: PRT
<213> ORGANISM: Artificial
<220> FEATURE:
<223> OTHER INFORMATION: Synthetic

<400> SEQUENCE: 6

Ala Ala Gln Thr Ser Thr Pro
1               5

<210> SEQ ID NO 7
<211> LENGTH: 7
<212> TYPE: PRT
<213> ORGANISM: Artificial
<220> FEATURE:
<223> OTHER INFORMATION: Synthetic

<400> SEQUENCE: 7

Tyr Gln Asp Ser Ala Lys Thr
1               5

<210> SEQ ID NO 8
<211> LENGTH: 7
<212> TYPE: PRT
<213> ORGANISM: Artificial
<220> FEATURE:
<223> OTHER INFORMATION: Synthetic

<400> SEQUENCE: 8

Ala Val Thr Ile Asn Glu Pro
1               5

<210> SEQ ID NO 9
<211> LENGTH: 7
<212> TYPE: PRT
<213> ORGANISM: Artificial
<220> FEATURE:
<223> OTHER INFORMATION: Synthetic

<400> SEQUENCE: 9

Val Thr Ala Ala Thr Leu Ser
1               5

<210> SEQ ID NO 10
<211> LENGTH: 7
<212> TYPE: PRT
<213> ORGANISM: Artificial
<220> FEATURE:
<223> OTHER INFORMATION: Synthetic

<400> SEQUENCE: 10

Thr Tyr Pro Ala Ala Leu Leu
1               5

<210> SEQ ID NO 11
<211> LENGTH: 7
<212> TYPE: PRT
<213> ORGANISM: Artificial
<220> FEATURE:
<223> OTHER INFORMATION: Synthetic
```

```
<400> SEQUENCE: 11

Glu Leu Ser Pro Ser Ala Pro
1               5

<210> SEQ ID NO 12
<211> LENGTH: 7
<212> TYPE: PRT
<213> ORGANISM: Artificial
<220> FEATURE:
<223> OTHER INFORMATION: Synthetic

<400> SEQUENCE: 12

Thr Val Pro Gln Leu Thr Thr
1               5

<210> SEQ ID NO 13
<211> LENGTH: 7
<212> TYPE: PRT
<213> ORGANISM: Artificial
<220> FEATURE:
<223> OTHER INFORMATION: Synthetic

<400> SEQUENCE: 13

Gln Asn Ala Pro Pro Ser Leu
1               5

<210> SEQ ID NO 14
<211> LENGTH: 7
<212> TYPE: PRT
<213> ORGANISM: Artificial
<220> FEATURE:
<223> OTHER INFORMATION: Synthetic

<400> SEQUENCE: 14

Tyr Asp Ile Asp Asn Arg Arg
1               5

<210> SEQ ID NO 15
<211> LENGTH: 7
<212> TYPE: PRT
<213> ORGANISM: Artificial
<220> FEATURE:
<223> OTHER INFORMATION: Synthetic

<400> SEQUENCE: 15

Gln Thr Leu Leu Pro Ser His
1               5

<210> SEQ ID NO 16
<211> LENGTH: 7
<212> TYPE: PRT
<213> ORGANISM: Artificial
<220> FEATURE:
<223> OTHER INFORMATION: Synthetic

<400> SEQUENCE: 16

Thr Ser Phe Gln Pro His Arg
1               5

<210> SEQ ID NO 17
<211> LENGTH: 7
<212> TYPE: PRT
<213> ORGANISM: Artificial
<220> FEATURE:
<223> OTHER INFORMATION: Synthetic

<400> SEQUENCE: 17
```

```
Gly Asn Thr Pro Ser Arg Ala
1               5

<210> SEQ ID NO 18
<211> LENGTH: 7
<212> TYPE: PRT
<213> ORGANISM: Artificial
<220> FEATURE:
<223> OTHER INFORMATION: Synthetic

<400> SEQUENCE: 18

Leu Thr Gln Met Ser Ile Ser
1               5

<210> SEQ ID NO 19
<211> LENGTH: 7
<212> TYPE: PRT
<213> ORGANISM: Artificial
<220> FEATURE:
<223> OTHER INFORMATION: Synthetic

<400> SEQUENCE: 19

Arg Leu Thr Leu Pro Met Pro
1               5

<210> SEQ ID NO 20
<211> LENGTH: 7
<212> TYPE: PRT
<213> ORGANISM: Artificial
<220> FEATURE:
<223> OTHER INFORMATION: Synthetic

<400> SEQUENCE: 20

Gly Thr Ala Pro Pro Val His
1               5

<210> SEQ ID NO 21
<211> LENGTH: 7
<212> TYPE: PRT
<213> ORGANISM: Artificial
<220> FEATURE:
<223> OTHER INFORMATION: Synthetic

<400> SEQUENCE: 21

His Ser Pro Ser Lys Ile Pro
1               5

<210> SEQ ID NO 22
<211> LENGTH: 7
<212> TYPE: PRT
<213> ORGANISM: Artificial
<220> FEATURE:
<223> OTHER INFORMATION: Synthetic

<400> SEQUENCE: 22

Phe Pro His Tyr Pro Met Ser
1               5

<210> SEQ ID NO 23
<211> LENGTH: 7
<212> TYPE: PRT
<213> ORGANISM: Artificial
<220> FEATURE:
<223> OTHER INFORMATION: Synthetic

<400> SEQUENCE: 23

Ala Ser His Leu Glu Pro Ser
1               5
```

```
<210> SEQ ID NO 24
<211> LENGTH: 7
<212> TYPE: PRT
<213> ORGANISM: Artificial
<220> FEATURE:
<223> OTHER INFORMATION: Synthetic

<400> SEQUENCE: 24

Ala Met Thr Thr Lys Ile Asp
1               5

<210> SEQ ID NO 25
<211> LENGTH: 7
<212> TYPE: PRT
<213> ORGANISM: Artificial
<220> FEATURE:
<223> OTHER INFORMATION: Synthetic

<400> SEQUENCE: 25

Ala Thr Leu Thr His Pro Pro
1               5

<210> SEQ ID NO 26
<211> LENGTH: 7
<212> TYPE: PRT
<213> ORGANISM: Artificial
<220> FEATURE:
<223> OTHER INFORMATION: Synthetic

<400> SEQUENCE: 26

His Met Ala Thr Phe His Tyr
1               5

<210> SEQ ID NO 27
<211> LENGTH: 7
<212> TYPE: PRT
<213> ORGANISM: Artificial
<220> FEATURE:
<223> OTHER INFORMATION: Synthetic

<400> SEQUENCE: 27

Leu Leu Ala Thr Pro Thr Pro
1               5

<210> SEQ ID NO 28
<211> LENGTH: 7
<212> TYPE: PRT
<213> ORGANISM: Artificial
<220> FEATURE:
<223> OTHER INFORMATION: Synthetic

<400> SEQUENCE: 28

Ala Gln Pro Asn Lys Phe Lys
1               5

<210> SEQ ID NO 29
<211> LENGTH: 7
<212> TYPE: PRT
<213> ORGANISM: Artificial
<220> FEATURE:
<223> OTHER INFORMATION: Synthetic

<400> SEQUENCE: 29

Met Pro Ala Leu Leu Arg Ser
1               5
```

```
<210> SEQ ID NO 30
<211> LENGTH: 7
<212> TYPE: PRT
<213> ORGANISM: Artificial
<220> FEATURE:
<223> OTHER INFORMATION: Synthetic

<400> SEQUENCE: 30

Leu Pro Pro Glu His Pro Leu
1               5

<210> SEQ ID NO 31
<211> LENGTH: 7
<212> TYPE: PRT
<213> ORGANISM: Artificial
<220> FEATURE:
<223> OTHER INFORMATION: Synthetic

<400> SEQUENCE: 31

Ala His Pro Gln Leu Ala Thr
1               5

<210> SEQ ID NO 32
<211> LENGTH: 7
<212> TYPE: PRT
<213> ORGANISM: Artificial
<220> FEATURE:
<223> OTHER INFORMATION: Synthetic

<400> SEQUENCE: 32

Tyr Ala Gly Pro Tyr Gln His
1               5

<210> SEQ ID NO 33
<211> LENGTH: 7
<212> TYPE: PRT
<213> ORGANISM: Artificial
<220> FEATURE:
<223> OTHER INFORMATION: Synthetic

<400> SEQUENCE: 33

His Trp Glu Met Trp Ser Tyr
1               5

<210> SEQ ID NO 34
<211> LENGTH: 7
<212> TYPE: PRT
<213> ORGANISM: Artificial
<220> FEATURE:
<223> OTHER INFORMATION: Synthetic

<400> SEQUENCE: 34

Gln Ala Pro Arg Leu Trp Ser
1               5

<210> SEQ ID NO 35
<211> LENGTH: 7
<212> TYPE: PRT
<213> ORGANISM: Artificial
<220> FEATURE:
<223> OTHER INFORMATION: Synthetic

<400> SEQUENCE: 35

His Thr Pro Asn Ser Thr His
1               5

<210> SEQ ID NO 36
<211> LENGTH: 7
```

```
<212> TYPE: PRT
<213> ORGANISM: Artificial
<220> FEATURE:
<223> OTHER INFORMATION: Synthetic

<400> SEQUENCE: 36

Ser Asn Gln Leu Val Glu Gly
1               5

<210> SEQ ID NO 37
<211> LENGTH: 7
<212> TYPE: PRT
<213> ORGANISM: Artificial
<220> FEATURE:
<223> OTHER INFORMATION: Synthetic

<400> SEQUENCE: 37

Phe Ser Pro Ser Thr Pro Asn
1               5

<210> SEQ ID NO 38
<211> LENGTH: 7
<212> TYPE: PRT
<213> ORGANISM: Artificial
<220> FEATURE:
<223> OTHER INFORMATION: Synthetic

<400> SEQUENCE: 38

Ala Ser Ser Pro Val His Arg
1               5

<210> SEQ ID NO 39
<211> LENGTH: 7
<212> TYPE: PRT
<213> ORGANISM: Artificial
<220> FEATURE:
<223> OTHER INFORMATION: Synthetic

<400> SEQUENCE: 39

Ser Pro His Ser Ala Ser Leu
1               5

<210> SEQ ID NO 40
<211> LENGTH: 7
<212> TYPE: PRT
<213> ORGANISM: Artificial
<220> FEATURE:
<223> OTHER INFORMATION: Synthetic

<400> SEQUENCE: 40

Asp Gln Leu Pro Leu Ile Pro
1               5

<210> SEQ ID NO 41
<211> LENGTH: 7
<212> TYPE: PRT
<213> ORGANISM: Artificial
<220> FEATURE:
<223> OTHER INFORMATION: Synthetic

<400> SEQUENCE: 41

Ser Leu Ala Ala Tyr Leu His
1               5

<210> SEQ ID NO 42
<211> LENGTH: 7
<212> TYPE: PRT
<213> ORGANISM: Artificial
```

```
<220> FEATURE:
<223> OTHER INFORMATION: Synthetic

<400> SEQUENCE: 42

Trp Ser Gln Met His Phe Leu
1               5

<210> SEQ ID NO 43
<211> LENGTH: 7
<212> TYPE: PRT
<213> ORGANISM: Artificial
<220> FEATURE:
<223> OTHER INFORMATION: Synthetic

<400> SEQUENCE: 43

Ser Ile Pro Leu Leu Asn His
1               5

<210> SEQ ID NO 44
<211> LENGTH: 7
<212> TYPE: PRT
<213> ORGANISM: Artificial
<220> FEATURE:
<223> OTHER INFORMATION: Synthetic

<400> SEQUENCE: 44

Asn Gln Gln Phe Tyr Ile Leu
1               5

<210> SEQ ID NO 45
<211> LENGTH: 7
<212> TYPE: PRT
<213> ORGANISM: Artificial
<220> FEATURE:
<223> OTHER INFORMATION: Synthetic

<400> SEQUENCE: 45

Phe Glu Ser Arg Leu Thr Ala
1               5

<210> SEQ ID NO 46
<211> LENGTH: 7
<212> TYPE: PRT
<213> ORGANISM: Artificial
<220> FEATURE:
<223> OTHER INFORMATION: Synthetic

<400> SEQUENCE: 46

Gln Pro Leu Ser Asn Ala Ser
1               5

<210> SEQ ID NO 47
<211> LENGTH: 7
<212> TYPE: PRT
<213> ORGANISM: Artificial
<220> FEATURE:
<223> OTHER INFORMATION: Synthetic

<400> SEQUENCE: 47

Lys Pro Ala Tyr Gly Ser Thr
1               5

<210> SEQ ID NO 48
<211> LENGTH: 7
<212> TYPE: PRT
<213> ORGANISM: Artificial
<220> FEATURE:
<223> OTHER INFORMATION: Synthetic
```

<400> SEQUENCE: 48

Ala Asn Tyr Ser Val Ser Ile
1               5

<210> SEQ ID NO 49
<211> LENGTH: 7
<212> TYPE: PRT
<213> ORGANISM: Artificial
<220> FEATURE:
<223> OTHER INFORMATION: Synthetic

<400> SEQUENCE: 49

Tyr Ser His Thr Ala Ala Thr
1               5

<210> SEQ ID NO 50
<211> LENGTH: 7
<212> TYPE: PRT
<213> ORGANISM: Artificial
<220> FEATURE:
<223> OTHER INFORMATION: Synthetic

<400> SEQUENCE: 50

Gln His Pro Pro Trp Arg Val
1               5

<210> SEQ ID NO 51
<211> LENGTH: 7
<212> TYPE: PRT
<213> ORGANISM: Artificial
<220> FEATURE:
<223> OTHER INFORMATION: Synthetic

<400> SEQUENCE: 51

Met Pro Ala Val Pro His Ser
1               5

<210> SEQ ID NO 52
<211> LENGTH: 7
<212> TYPE: PRT
<213> ORGANISM: Artificial
<220> FEATURE:
<223> OTHER INFORMATION: Synthetic

<400> SEQUENCE: 52

Ser Ala Leu Leu Pro Ser Phe
1               5

<210> SEQ ID NO 53
<211> LENGTH: 7
<212> TYPE: PRT
<213> ORGANISM: Artificial
<220> FEATURE:
<223> OTHER INFORMATION: Synthetic

<400> SEQUENCE: 53

Thr His Pro Pro Thr Thr His
1               5

<210> SEQ ID NO 54
<211> LENGTH: 7
<212> TYPE: PRT
<213> ORGANISM: Artificial
<220> FEATURE:
<223> OTHER INFORMATION: Synthetic

<400> SEQUENCE: 54

Ser Asn Ser Ile Arg Pro Asn
1               5

<210> SEQ ID NO 55
<211> LENGTH: 7
<212> TYPE: PRT
<213> ORGANISM: Artificial
<220> FEATURE:
<223> OTHER INFORMATION: Synthetic

<400> SEQUENCE: 55

Ala Ser Val Gln Gln Arg Gly
1               5

<210> SEQ ID NO 56
<211> LENGTH: 7
<212> TYPE: PRT
<213> ORGANISM: Artificial
<220> FEATURE:
<223> OTHER INFORMATION: Synthetic

<400> SEQUENCE: 56

Phe Pro Pro Ser Phe Thr Ala
1               5

<210> SEQ ID NO 57
<211> LENGTH: 7
<212> TYPE: PRT
<213> ORGANISM: Artificial
<220> FEATURE:
<223> OTHER INFORMATION: Synthetic

<400> SEQUENCE: 57

Met Gln Gln Gly Pro Arg Pro
1               5

<210> SEQ ID NO 58
<211> LENGTH: 7
<212> TYPE: PRT
<213> ORGANISM: Artificial
<220> FEATURE:
<223> OTHER INFORMATION: Synthetic

<400> SEQUENCE: 58

Gln Lys Thr Ala Leu Pro Leu
1               5

<210> SEQ ID NO 59
<211> LENGTH: 7
<212> TYPE: PRT
<213> ORGANISM: Artificial
<220> FEATURE:
<223> OTHER INFORMATION: Synthetic

<400> SEQUENCE: 59

Thr Tyr Gly Thr Lys Ile Ser
1               5

<210> SEQ ID NO 60
<211> LENGTH: 7
<212> TYPE: PRT
<213> ORGANISM: Artificial
<220> FEATURE:
<223> OTHER INFORMATION: Synthetic

<400> SEQUENCE: 60

Ser Leu Lys Leu Leu Asn Gln

```
<210> SEQ ID NO 61
<211> LENGTH: 7
<212> TYPE: PRT
<213> ORGANISM: Artificial
<220> FEATURE:
<223> OTHER INFORMATION: Synthetic

<400> SEQUENCE: 61

Thr Ser Ser Thr Met Asn Arg
1               5

<210> SEQ ID NO 62
<211> LENGTH: 7
<212> TYPE: PRT
<213> ORGANISM: Artificial
<220> FEATURE:
<223> OTHER INFORMATION: Synthetic

<400> SEQUENCE: 62

Tyr Lys His Thr Pro Thr Thr
1               5

<210> SEQ ID NO 63
<211> LENGTH: 7
<212> TYPE: PRT
<213> ORGANISM: Artificial
<220> FEATURE:
<223> OTHER INFORMATION: Synthetic

<400> SEQUENCE: 63

Gly Ser Trp Tyr Gln Val Pro
1               5

<210> SEQ ID NO 64
<211> LENGTH: 7
<212> TYPE: PRT
<213> ORGANISM: Artificial
<220> FEATURE:
<223> OTHER INFORMATION: Synthetic

<400> SEQUENCE: 64

Tyr Tyr Phe Pro Pro Phe Tyr
1               5

<210> SEQ ID NO 65
<211> LENGTH: 7
<212> TYPE: PRT
<213> ORGANISM: Artificial
<220> FEATURE:
<223> OTHER INFORMATION: Synthetic

<400> SEQUENCE: 65

Ala Tyr Lys Pro Val Gly Arg
1               5

<210> SEQ ID NO 66
<211> LENGTH: 7
<212> TYPE: PRT
<213> ORGANISM: Artificial
<220> FEATURE:
<223> OTHER INFORMATION: Synthetic

<400> SEQUENCE: 66

Ala Ser Thr Leu Lys Trp Ala
1               5
```

<210> SEQ ID NO 67
<211> LENGTH: 7
<212> TYPE: PRT
<213> ORGANISM: Artificial
<220> FEATURE:
<223> OTHER INFORMATION: Synthetic

<400> SEQUENCE: 67

Thr Trp Thr Phe Arg Ile Pro
1               5

<210> SEQ ID NO 68
<211> LENGTH: 7
<212> TYPE: PRT
<213> ORGANISM: Artificial
<220> FEATURE:
<223> OTHER INFORMATION: Synthetic

<400> SEQUENCE: 68

Ser Tyr Met Ile Gln Leu Ser
1               5

<210> SEQ ID NO 69
<211> LENGTH: 7
<212> TYPE: PRT
<213> ORGANISM: Artificial
<220> FEATURE:
<223> OTHER INFORMATION: Synthetic

<400> SEQUENCE: 69

Ile Gln Ser Pro His Phe Phe
1               5

<210> SEQ ID NO 70
<211> LENGTH: 7
<212> TYPE: PRT
<213> ORGANISM: Artificial
<220> FEATURE:
<223> OTHER INFORMATION: Synthetic

<400> SEQUENCE: 70

Ser Val Ser Pro Trp Gly Ile
1               5

<210> SEQ ID NO 71
<211> LENGTH: 7
<212> TYPE: PRT
<213> ORGANISM: Artificial
<220> FEATURE:
<223> OTHER INFORMATION: Synthetic

<400> SEQUENCE: 71

Thr His Leu Pro Trp Gln Thr
1               5

<210> SEQ ID NO 72
<211> LENGTH: 7
<212> TYPE: PRT
<213> ORGANISM: Artificial
<220> FEATURE:
<223> OTHER INFORMATION: Synthetic

<400> SEQUENCE: 72

Ala His Ser Met Gly Thr Gly
1               5

<210> SEQ ID NO 73

```
<211> LENGTH: 7
<212> TYPE: PRT
<213> ORGANISM: Artificial
<220> FEATURE:
<223> OTHER INFORMATION: Synthetic

<400> SEQUENCE: 73

Phe Met Ser Pro Leu Trp Thr
1               5

<210> SEQ ID NO 74
<211> LENGTH: 7
<212> TYPE: PRT
<213> ORGANISM: Artificial
<220> FEATURE:
<223> OTHER INFORMATION: Synthetic

<400> SEQUENCE: 74

Ile Val Asn Thr Ala Pro Leu
1               5

<210> SEQ ID NO 75
<211> LENGTH: 7
<212> TYPE: PRT
<213> ORGANISM: Artificial
<220> FEATURE:
<223> OTHER INFORMATION: Synthetic

<400> SEQUENCE: 75

Ser Thr Phe Thr Lys Ser Pro
1               5

<210> SEQ ID NO 76
<211> LENGTH: 7
<212> TYPE: PRT
<213> ORGANISM: Artificial
<220> FEATURE:
<223> OTHER INFORMATION: Synthetic

<400> SEQUENCE: 76

Ile Pro Thr Leu Pro Ser Ser
1               5

<210> SEQ ID NO 77
<211> LENGTH: 7
<212> TYPE: PRT
<213> ORGANISM: Artificial
<220> FEATURE:
<223> OTHER INFORMATION: Synthetic

<400> SEQUENCE: 77

Ala Phe Val Ser Arg Gln Pro
1               5

<210> SEQ ID NO 78
<211> LENGTH: 7
<212> TYPE: PRT
<213> ORGANISM: Artificial
<220> FEATURE:
<223> OTHER INFORMATION: Synthetic

<400> SEQUENCE: 78

Ser Ser Leu Pro Leu Arg Lys
1               5

<210> SEQ ID NO 79
<211> LENGTH: 7
<212> TYPE: PRT
```

```
<213> ORGANISM: Artificial
<220> FEATURE:
<223> OTHER INFORMATION: Synthetic

<400> SEQUENCE: 79

Thr Tyr Ser Thr Leu Gly Tyr
1               5

<210> SEQ ID NO 80
<211> LENGTH: 7
<212> TYPE: PRT
<213> ORGANISM: Artificial
<220> FEATURE:
<223> OTHER INFORMATION: Synthetic

<400> SEQUENCE: 80

Val Thr Tyr Lys Thr Ala Ser
1               5

<210> SEQ ID NO 81
<211> LENGTH: 7
<212> TYPE: PRT
<213> ORGANISM: Artificial
<220> FEATURE:
<223> OTHER INFORMATION: Synthetic

<400> SEQUENCE: 81

Glu Pro Leu Gln Leu Lys Met
1               5

<210> SEQ ID NO 82
<211> LENGTH: 7
<212> TYPE: PRT
<213> ORGANISM: Artificial
<220> FEATURE:
<223> OTHER INFORMATION: Synthetic

<400> SEQUENCE: 82

Trp Ser Leu Gln Ala Ser His
1               5

<210> SEQ ID NO 83
<211> LENGTH: 7
<212> TYPE: PRT
<213> ORGANISM: Artificial
<220> FEATURE:
<223> OTHER INFORMATION: Synthetic

<400> SEQUENCE: 83

Thr Leu Trp Val Pro Ser Arg
1               5

<210> SEQ ID NO 84
<211> LENGTH: 7
<212> TYPE: PRT
<213> ORGANISM: Artificial
<220> FEATURE:
<223> OTHER INFORMATION: Synthetic

<400> SEQUENCE: 84

Gln Gly Met His Arg Gly Thr
1               5

<210> SEQ ID NO 85
<211> LENGTH: 7
<212> TYPE: PRT
<213> ORGANISM: Artificial
<220> FEATURE:
```

```
<223> OTHER INFORMATION: Synthetic

<400> SEQUENCE: 85

Leu Tyr Gln Asp Tyr Ser Leu
1               5

<210> SEQ ID NO 86
<211> LENGTH: 7
<212> TYPE: PRT
<213> ORGANISM: Artificial
<220> FEATURE:
<223> OTHER INFORMATION: Synthetic

<400> SEQUENCE: 86

Ser Glu Ser Met Ser Ile Lys
1               5

<210> SEQ ID NO 87
<211> LENGTH: 7
<212> TYPE: PRT
<213> ORGANISM: Artificial
<220> FEATURE:
<223> OTHER INFORMATION: Synthetic

<400> SEQUENCE: 87

Leu Pro Trp Lys Pro Leu Gly
1               5

<210> SEQ ID NO 88
<211> LENGTH: 7
<212> TYPE: PRT
<213> ORGANISM: Artificial
<220> FEATURE:
<223> OTHER INFORMATION: Synthetic

<400> SEQUENCE: 88

Gln Ser Pro His Thr Ala Pro
1               5

<210> SEQ ID NO 89
<211> LENGTH: 7
<212> TYPE: PRT
<213> ORGANISM: Artificial
<220> FEATURE:
<223> OTHER INFORMATION: Synthetic

<400> SEQUENCE: 89

Thr Pro Ala His Pro Asn Tyr
1               5

<210> SEQ ID NO 90
<211> LENGTH: 7
<212> TYPE: PRT
<213> ORGANISM: Artificial
<220> FEATURE:
<223> OTHER INFORMATION: Synthetic

<400> SEQUENCE: 90

Ser Leu Leu Gly Ser Thr Pro
1               5

<210> SEQ ID NO 91
<211> LENGTH: 7
<212> TYPE: PRT
<213> ORGANISM: Artificial
<220> FEATURE:
<223> OTHER INFORMATION: Synthetic
```

```
<400> SEQUENCE: 91

Thr Ala Leu Pro Pro Ser Tyr
1               5

<210> SEQ ID NO 92
<211> LENGTH: 7
<212> TYPE: PRT
<213> ORGANISM: Artificial
<220> FEATURE:
<223> OTHER INFORMATION: Synthetic

<400> SEQUENCE: 92

Val Asn Ser Ala Thr His Ser
1               5

<210> SEQ ID NO 93
<211> LENGTH: 7
<212> TYPE: PRT
<213> ORGANISM: Artificial
<220> FEATURE:
<223> OTHER INFORMATION: Synthetic

<400> SEQUENCE: 93

Leu Pro Leu Thr Pro Leu Pro
1               5

<210> SEQ ID NO 94
<211> LENGTH: 7
<212> TYPE: PRT
<213> ORGANISM: Artificial
<220> FEATURE:
<223> OTHER INFORMATION: Synthetic

<400> SEQUENCE: 94

Asn Gln Leu Pro Leu His Ala
1               5

<210> SEQ ID NO 95
<211> LENGTH: 7
<212> TYPE: PRT
<213> ORGANISM: Artificial
<220> FEATURE:
<223> OTHER INFORMATION: Synthetic

<400> SEQUENCE: 95

Thr Gln Thr Pro Leu Lys Gln
1               5

<210> SEQ ID NO 96
<211> LENGTH: 7
<212> TYPE: PRT
<213> ORGANISM: Artificial
<220> FEATURE:
<223> OTHER INFORMATION: Synthetic

<400> SEQUENCE: 96

His Ala Ile Tyr Pro Arg His
1               5

<210> SEQ ID NO 97
<211> LENGTH: 7
<212> TYPE: PRT
<213> ORGANISM: Artificial
<220> FEATURE:
<223> OTHER INFORMATION: Synthetic

<400> SEQUENCE: 97
```

```
Ala Met Ile Ser Ala Ile His
1               5

<210> SEQ ID NO 98
<211> LENGTH: 7
<212> TYPE: PRT
<213> ORGANISM: Artificial
<220> FEATURE:
<223> OTHER INFORMATION: Synthetic

<400> SEQUENCE: 98

Asn Leu Thr Arg Leu His Thr
1               5

<210> SEQ ID NO 99
<211> LENGTH: 7
<212> TYPE: PRT
<213> ORGANISM: Artificial
<220> FEATURE:
<223> OTHER INFORMATION: Synthetic

<400> SEQUENCE: 99

His Val Ile Ala Asn Ala Gly
1               5

<210> SEQ ID NO 100
<211> LENGTH: 7
<212> TYPE: PRT
<213> ORGANISM: Artificial
<220> FEATURE:
<223> OTHER INFORMATION: Synthetic

<400> SEQUENCE: 100

Leu Gly Ala Gln Ser Asn Phe
1               5

<210> SEQ ID NO 101
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 101

Lys Lys Lys Arg
1

<210> SEQ ID NO 102
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 102

Lys Lys Arg Lys
1

<210> SEQ ID NO 103
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 103

Lys Lys Lys Arg Lys
1               5
```

<210> SEQ ID NO 104
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 104

Lys Lys Arg Ser
1

<210> SEQ ID NO 105
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 105

Lys Arg Ser Lys
1

<210> SEQ ID NO 106
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 106

Lys Lys Arg Ser Lys
1               5

<210> SEQ ID NO 107
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 107

Lys Ser Arg Lys
1

<210> SEQ ID NO 108
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 108

Ser Arg Lys Arg
1

<210> SEQ ID NO 109
<211> LENGTH: 4
<212> TYPE: PRT
<213> ORGANISM: Artificial
<220> FEATURE:
<223> OTHER INFORMATION: Synthetic, Nuclear Localisation Signal

<400> SEQUENCE: 109

Arg Lys Arg Lys
1

```
<210> SEQ ID NO 110
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 110

Lys Ser Arg Lys Arg
1               5

<210> SEQ ID NO 111
<211> LENGTH: 5
<212> TYPE: PRT
<213> ORGANISM: Artificial
<220> FEATURE:
<223> OTHER INFORMATION: Synthetic, Nuclear Localisation Signal

<400> SEQUENCE: 111

Ser Arg Lys Arg Lys
1               5

<210> SEQ ID NO 112
<211> LENGTH: 6
<212> TYPE: PRT
<213> ORGANISM: Artificial
<220> FEATURE:
<223> OTHER INFORMATION: Synthetic, Nuclear Localisation Signal

<400> SEQUENCE: 112

Lys Ser Arg Lys Arg Lys
1               5

<210> SEQ ID NO 113
<211> LENGTH: 7
<212> TYPE: PRT
<213> ORGANISM: Artificial
<220> FEATURE:
<223> OTHER INFORMATION: Synthetic, Nuclear Localisation Signal

<400> SEQUENCE: 113

Pro Lys Lys Lys Arg Lys Val
1               5

<210> SEQ ID NO 114
<211> LENGTH: 7
<212> TYPE: PRT
<213> ORGANISM: Artificial
<220> FEATURE:
<223> OTHER INFORMATION: Synthetic, Nuclear Localisation Signal

<400> SEQUENCE: 114

Gly Lys Lys Arg Ser Lys Val
1               5

<210> SEQ ID NO 115
<211> LENGTH: 7
<212> TYPE: PRT
<213> ORGANISM: Artificial
<220> FEATURE:
<223> OTHER INFORMATION: Synthetic, Nuclear Localisation Signal

<400> SEQUENCE: 115

Lys Ser Arg Lys Arg Lys Leu
1               5
```

MOLECULES FOR TARGETING COMPOUNDS TO VARIOUS SELECTED ORGANS OR TISSUES

RELATED APPLICATIONS

This application is a Divisional of U.S. application Ser. No. 12/685,369, filed on Jan. 11, 2010, which claims priority to PCT international application Ser. No. PCT/NL2008/050475, filed Jul. 14, 2008, designating the United States, which claims the benefit of European patent application No. 07112323.6, filed on Jul. 12, 1007. The entire contents of the aforementioned patent applications are incorporated herein by this reference.

FIELD OF THE INVENTION

The present invention is in the field of in vivo targeting and provides molecules that home to, bind to and are taken up by various organs or tissues.

BACKGROUND OF THE INVENTION

Most therapeutic compounds are delivered to the target organ or tissue through the circulation. However, in most cases the drug or other treatment will not only target the diseased organ or tissues, but will also be taken up by other organs and tissues in the body. This can result in undesirable side effects due to, for example, generalized toxic effects throughout the patient's body. Thus, it would be desirable to selectively target specific organs or tissues. In addition, coupling of a therapeutic compound to a targeting molecule can improve the uptake properties of the compound into the targeted tissue or cells, resulting in a more effective molecule. Therefore, coupling to targeting molecules yields compounds that are more effective and less toxic than the parental compound, see Curnis et al., 2000, Nature Biotechnol. 18, 1185-1190. This can be applied to a wide range of compounds, such as peptides, proteins, cytostatic agents, antibiotic and antiviral agents.

In the case of muscle diseases such as Duchenne muscular dystrophy (DMD), myotonic dystrophy (MD) or spinal muscular atrophy (SMA), muscle-specific peptides can be conjugated to, for example, antisense oligonucleotides (AONs) and small interfering RNA (siRNA). AONs and siRNAs have high potency to be applied as new classes of medicines for treatment of specific diseases by blocking undesired gene transcription. In the field of DMD therapy antisense-induced exon skipping is gaining attention as a novel and promising tool for correction of the translational reading frame of the dystrophin transcript. The aim is to manipulate splicing in such a manner that the targeted exon will be skipped (through binding of the AONs to pre-mRNA) and a slightly shorter but in-frame transcript will be generated. This would allow correction of the translational reading frame, and induction of the synthesis of a Becker muscular dystrophy (BMD)-like dystrophin protein that may significantly alleviate progression of the disease.

Several reports have shown the therapeutic potential of the exon skipping strategy for restoring dystrophin production in cultured patient-derived muscle cells in vitro (van Deutekom et al., 2001, Hum. Mol. Genet. 10, 1547-1554) and in transgenic hDMD mouse muscle tissue in vivo by intramuscular injections (Bremmer-Bout et al., 2004, Mol. Ther. 10, 232-240). However, the biggest hurdle to overcome is the poor in vivo muscle uptake of these AONs, especially in all kind of myopathies like Myotonic Dystrophy (MD) and Spinal Muscular Atrophy (SMA).

An efficient therapy for these muscle wasting diseases will require that essentially all of the skeletal muscles including those of arms and legs and the muscles involved in respiration as well as the cardiac muscle are targeted. None of the mechanisms investigated to date have the ability to specifically deliver (antisense) oligonucleotides, let alone entire genes, to essentially all muscle tissues/cells simultaneously over the entire body. Methods for the in vivo delivery of genes or other compounds into muscle that have been published so far include injection of naked DNA with or without electrotransfer, use of microbubbles (Lu et al. 2003, Gene Ther. 10, 396-405) and systemic delivery using poloxamer (a hydroxypoly(oxy-ethylene)poly(oxypropylene)). Recently it was shown in mdx mice that systemic delivery of morpholino AONs resulted in an increased dystrophin expression in several muscles (Alter et al., 2006, Nature Med. 12, 1-3). However, even after repeated administration, dystrophin expression was barely detectable in diaphragm and was undetectable in heart muscle. Furthermore, in these mdx mice the AONs are taken up rather easy into the muscles because the muscle membranes are compromised, which is not the case for the muscles of, for instance, young Duchenne patients. Also, in other muscle diseases like SMA and MD delivery of AON is complicated due to the fact that in this case the muscle cell walls are not compromised.

Ideally, whole-body muscle therapy would use systemic delivery (e.g. intravenously or subcutaneously) of a compound endowed with a cell specific targeting ability. Some molecules have been described that have potential for muscle cell targeting. The first report is of a peptide sequence with enhanced in vivo skeletal and cardiac muscle binding, that was identified by screening a random phage display library (Samoylova and Smith, 1999, Muscle Nerve 22, 460-466). However, it has not yet been shown whether or not this peptide can be used for in vivo targeting of conjugated compounds to muscle cells. Also a number of 7-mer peptide sequences that were recovered from human skeletal muscle after in vivo screening of phage random peptide library have been described (Arap et al., 2002, Nature Medicine 8, 121-127). No information is given on binding to cardiac muscle cells. Also here it has not yet been shown whether or not these peptides can be used for in vivo targeting of conjugated compounds to muscle cells. Another molecule that has been described is an Fv part of a monoclonal antibody (mAb) that is selectively transported into skeletal muscle in vivo (Weisbart et al., 2003, Mol. Immunol. 39, 783-789). Single chain Fv fragments of the murine mAb were injected into the tail veins of mice and 4 hours later the fragments were found in 20% of skeletal muscle cells, primarily localized in the nucleus. It was shown that the mAb binds to the protein myosin IIb in lysates of skeletal muscle cells, but it did not bind any protein in lysates of heart muscle cells. Therefore, this antibody might be useful for targeting to skeletal muscles, but not to the heart muscle.

In the case of lysosomal storage disease a problem in the enzyme replacement therapy is poor in vivo uptake of the therapeutic recombinant enzyme into the muscle cells. For example in Pompe's disease (glycogen storage disease type II) the doses of recombinant human acid α-glucosidase (rhGAA) that were needed in clinical studies were very high, due to poor uptake of the rhGAA into the skeletal muscle (Winkel et al., 2004, Ann. Neurol. 55, 495-502). In light of the above, it is very clear that further improvements in delivery systems are necessary to achieve specific uptake of agents such as AONs in vivo.

SUMMARY OF THE INVENTION

It is an object of the present invention to provide compounds, preferably peptides or peptidomimetics, that home to an organ or tissue or cell type of interest, especially muscle cells including the heart. By coupling diagnostic moieties or moieties having a biological activity to such homing compounds, said moieties are targeted to the specific organs or tissues or cells.

After extensive research, the present inventors have identified a number of peptides that selectively bind to and are taken up by muscle cells, including the heart. This invention thus fulfills the need of improving the in vivo uptake of for example therapeutic recombinant enzyme or (anti-sense) oligonucleotides, by conjugation of such enzyme or oligonucleotides to muscle-specific peptides. The molecules are advantageously useful in anti-sense therapy methods for treatment of myopathies, gene therapy of disease where muscles potentially serve as reservoirs of protein production and delivery of a wide variety of diagnostics or drugs to heart and muscle cells.

Thus the present invention relates to a peptide or peptidomimetic comprising a sequence or consisting of a sequence selected form the group consisting of

```
                                          (SEQ ID NO: 100)
LGAQSNF (SEQ ID NO: 3)
QLFTSAS (SEQ ID NO: 85)
LYQDYSL

SPNSIGT STFTHPR         STIHGST SAPRPLY

AAQTSTP YQDSAKT AVTINEP VTAATLS TYPAALL

ELSPSAP TVPQLTT QNAPPSL YDIDNRR QTLLPSH

TSFQPHR GNTPSRA LTQMSIS RLTLPMP GTAPPVH

HSPSKIP FPHYPMS ASHLEPS AMTTKID ATLTHPP

HMATFHY LLATPTP AQPNKFK MPALLRS LPPEHPL

AHPQLAT YAGPYQH HWEMWSY QAPRLWS HTPNSTH

SNQLVEG FSPSTPN ASSPVHR SPHSASL DQLPLIP

SLAAYLH WSQMHFL SIPLLNH NQQFYIL FESRLTA

QPLSNAS KPAYGST ANYSVSI YSHTAAT QHPPWRV

MPAVPHS SALLPSF THPPTTH SNSIRPN ASVQQRG

FPPSFTA MQQGPRP QKTALPL TYGTKIS SLKLLNQ

TSSTMNR YKHTPTT GSWYQVP YYFPPFY AYKPVGR

ASTLKWA TWTFRIP SYMIQLS IQSPHFF SVSPWGI

THLPWQT AHSMGTG FMSPLWT IVNTAPL STFTKSP

IPTLPSS AFVSRQP SSLPLRK TYSTLGY VTYKTAS

EPLQLKM WSLQASH TLWVPSR QGMHRGT

SESMSIK LPWKPLG QSPHTAP TPAHPNY SLLGSTP
```

```
-continued
TALPPSY VNSATHS LPLTPLP NQLPLHA TQTPLKQ

HAIYPRH AMISAIH NLTRLHT HVIANAG
```

The group above has the sequence identifiers SEQ ID NO: 1-SEQ ID NO: 100.

Also the present invention concerns conjugates of a peptide or peptidomimetics comprising a sequence or consisting of a sequence selected form the group consisting of

```
                                          (SEQ ID NO: 100)
LGAQSNF (SEQ ID NO: 3)
QLFTSAS (SEQ ID NO: 85)
LYQDYSL

SPNSIGT STFTHPR         STIHGST SAPRPLY

AAQTSTP YQDSAKT AVTINEP VTAATLS TYPAALL

ELSPSAP TVPQLTT QNAPPSL YDIDNRR QTLLPSH

TSFQPHR GNTPSRA LTQMSIS RLTLPMP GTAPPVH

HSPSKIP FPHYPMS ASHLEPS AMTTKID ATLTHPP

HMATFHY LLATPTP AQPNKFK MPALLRS LPPEHPL

AHPQLAT YAGPYQH HWEMWSY QAPRLWS HTPNSTH

SNQLVEG FSPSTPN ASSPVHR SPHSASL DQLPLIP

SLAAYLH WSQMHFL SIPLLNH NQQFYIL FESRLTA

QPLSNAS KPAYGST ANYSVSI YSHTAAT QHPPWRV

MPAVPHS SALLPSF THPPTTH SNSIRPN ASVQQRG

FPPSFTA MQQGPRP QKTALPL TYGTKIS SLKLLNQ

TSSTMNR YKHTPTT GSWYQVP YYFPPFY AYKPVGR

ASTLKWA TWTFRIP SYMIQLS IQSPHFF SVSPWGI

THLPWQT AHSMGTG FMSPLWT IVNTAPL STFTKSP

IPTLPSS AFVSRQP SSLPLRK TYSTLGY VTYKTAS

EPLQLKM WSLQASH TLWVPSR QGMHRGT

SESMSIK LPWKPLG QSPHTAP TPAHPNY SLLGSTP

TALPPSY VNSATHS LPLTPLP NQLPLHA TQTPLKQ

HAIYPRH AMISAIH NLTRLHT HVIANAG
``` and a moiety selected from a biologically active moiety and diagnostic moiety linked thereto.

A conjugate as described above for use as a medicament is an aspect of this invention.

DETAILED DESCRIPTION OF THE INVENTION

The present invention provides peptides or peptidomimetics for targeting diagnostic moieties or biologically active moieties to an organ or tissue or cell type of interest, especially muscle cells including the heart.

A peptide in the context of this invention comprises at least 7 amino acids. The peptide can be fully constructed of naturally occurring L-amino acids, or can contain one or more modifications to backbone and/or side chain(s). These modifications can be introduced by incorporation of amino acid mimetics that show similarity to the natural amino acid. The group of peptides described above comprising one or more mimetics of amino acids is referred to as peptidomimetics. In the context of this invention, mimetics of amino acids include, but are not limited to, β2- and β3-amino acids, β2,2-β2,3, and β3,3-disubstituted amino acids, α,α-disubstituted amino acids, statine derivatives of amino acids, D-amino acids, α-hydroxyacids, α-aminonitriles, N-alkylamino acids and the like. In addition, the C-terminus of the peptide might be carboxylic acid or carboxamide, or other resulting from incorporation of one of the above mentioned amino acid mimetics. Furthermore, the peptides described above may contain one or more replacements of native peptide bonds with groups including, but not limited to, sulfonamide, retroamide, aminooxy-containing bond, ester, alkylketone, α,β-difluoroketone, α-fluoroketone, peptoid bond (N-alkylated glycyl amide bond). Furthermore, the peptides mentioned above may contain substitutions in the amino acid side chain (referring to the side chain of the corresponding natural amino acid), for instance 4-fluorophenylalanine, 4-hydroxylysine, 3-aminoproline, 2-nitrotyrosine, N-alkylhistidine or β-branched amino acids or β-branched amino acid mimetics with chirality at the β-side chain carbon atom opposed to the natural chirality (e.g. allo-threonine, allo-isoleucine and derivatives). In one other embodiment, above mentioned group of peptides may contain close structural analogues of amino acid or amino acids mimetics, for instance ornithine instead of lysine, homophenylalanine or phenylglycine instead of phenylalanine, β-alanine instead of glycine, pyroglutamic acid instead of glutamic acid, norleucine instead of leucine or the sulfur-oxidized versions of methionine and/or cysteine. The linear and cyclized forms of the peptides mentioned above are covered by this patent, as well as their retro, inverso and/or retroinverso analogues. To those skilled in the art many more close variations may be known, but the fact that these are not mentioned here does not limit the scope of the present invention. In one embodiment, a peptide or peptidomimetic according to the present invention is at most 30 amino acids in length, or at least 25 amino acids or 20 amino acids or 19, 18, 17, 16, 15, 14, 13, 12, 11, 10, 9, 8 or 7 amino acids in length.

A biologically active moiety is a compound exerting (directly or indirectly) a biological function, preferably a therapeutic function, hence is preferably a therapeutically active compound. A therapeutically active compound can be any compound known in the art and preferably is a compound that has a therapeutic effect by modulating an intercellular process. A therapeutically active compound that has a (direct) modulating effect or (direct) biological function can be for instance any protein, enzyme inhibitor, oligonucleotide, siRNA, gene, or pharmaceutical. Any biologically active compound or therapeutically active compound can be used as long as it can be linked to or can be made suitable to be linked to a peptide or peptidomimetic according to the present invention. The biologically active compound or therapeutically active compound so becomes the moiety in the compound according to the present invention. The skilled person will be able to identify suitable biologically active or therapeutically active compounds.

In one embodiment the biologically active compound or therapeutically active compound is a compound comprising or consisting of nucleic acids or analogues thereof. Such compounds can be considered to exert (indirectly) a biological function, preferably a therapeutic function, by modulating the genetic machinery within a cell, in particular on the level of production of proteins. The nucleic acid may be a DNA, RNA or analogues thereof, such as compounds comprising 2'-O-alkyl or 2'-O-alkenyl (allyl) or 2'-O-alkynyl nucleotides, e.g. 2'-O-methyl-, 2'-O-methoxyethyl-(MOE) and 2'-O-allyl-nucleotides, locked nucleic acids (LNAs), peptide nucleic acids (PNAs), ethylene bridged nucleic acids (ENAs), phosphorothioate modified nucleotides, e.g. 2'-O-methoxyethyl phosphorothioate RNA nucleotides or 2'-O-methyl phosphorothioate RNA nucleotides, morpholino based nucleotides and combinations thereof etc. The nucleic acid may be a gene, a polynucleotide or oligonucleotide, small interfering RNA and the like.

In one embodiment a diagnostic moiety is linked to the peptides or peptidomimetics according to the present invention. The diagnostic moiety may be for in vivo or in vitro diagnostic purposes. Commonly used imaging labels, radio labels or fluorescent labels such as Cy3, Cy5, Cy5.5 and the like, or green fluorescent protein (GFP) or other diagnostic proteins, possibly via recombinant expression may be used as diagnostic moieties.

In order to prepare the conjugates according to the present invention, coupling of the biologically active moiety or diagnostic moiety to the peptides or peptidomimetics according to the present invention occurs via known methods to couple compounds to amino acids or peptides. A common method is to link a moiety to a free amino group or free hydroxyl group or free carboxylic acid group or free thiol group in a peptide or peptidomimetic. Common conjugation methods include thiol/maleimide coupling, amide or ester bond formation, or heterogeneous disulfide formation. The skilled person is well aware of standard chemistry that can be used to bring about the required coupling. The biologically active moiety or diagnostic moiety may be coupled directly to a peptide or peptidomimetic or may be coupled via a spacer or linker molecule. It is not necessary that the biologically active or diagnostic moiety is covalently linked to the peptide or petidomimetic of the invention. It may also be conjugated via electrostatic interactions. In one embodiment the present invention also relates to a molecule comprising a peptide or peptidomimetic according to the invention and a linking part, which is not a peptide, for linking the molecule to a biologically active moiety or a diagnostic moiety. The linking part for example may be a (poly)cationic group that complexes with a biologically active poly- or oligonucleotide. Such a (poly)cationic group may be a spermine or polyethyleneimine, polyethylene glycol, poly-L-lysine and the like.

As mentioned in one embodiment the peptide or peptidomimetic according to the present invention is linked to a biologically active moiety. For example the peptide or peptidomimetic can be linked to a biologically active or therapeutic peptide and in one embodiment can even be part of the peptide or peptidomimetic basic structure. For example the amino- or carboxy-terminus of a therapeutic peptide can be extended with a sequence comprising or consisting of the peptides described above. It is to be understood that such a peptide extended with a peptide or peptidomimetic according to the invention is encompassed by a conjugate according to the present invention. The preparation of such peptides can be achieved via standard amino acid or peptide coupling procedures.

In one embodiment the peptide or peptidomimetic according to the present invention is combined with a nuclear localization signal (NLS). In one embodiment a conjugate according to the present invention is combined with a NLS. In the context of the present invention the NLS functions to direct the present conjugates, e.g. the biologically active moiety or a diagnostic moiety, into a cell nucleus, presumably via its recognition by cytosolic nuclear transport receptors. The NLS may be part of the peptide or peptidomimetic according to the present invention, e.g. the amino- or carboxy-terminus of a NLS can be extended with a sequence comprising or consisting of the peptides described above. Also a NLS may be coupled at a different position than that of the peptide or peptidomimetic according to the present invention to a biologically active moiety or a diagnostic moiety. NLS sequences are known in the art. Typically a NLS signal consists of or comprises (a few) short sequences of positively charged lysines and/or arginines, for example a NLS consist of or comprises (K)KKR(K), (K)KRS(K), (K)(S)RK(R)(K). Known NLS are PKKKRKV, GKKRSKV, KSRKRKL. In one embodiment the peptide or peptidomimetic according to the present invention is combined with a NLS selected from the group consisting of SEQ ID NO: 101-115.

In one embodiment a conjugate according to the invention wherein the biologically active moiety is a protein or polypeptide and wherein the peptide or peptidomimetic is comprised in the protein or polypeptide backbone is prepared by recombinant expression of the peptide or peptidomimetic together with the biologically active protein. Preferably a DNA construct is prepared such that the peptide or peptidomimetic according to the invention is expressed at a terminus of the biologically active peptide, preferably at the C-terminus of the biologically active peptide. Such preparation of DNA constructs by recombinant DNA methodology and expression in a suitable host is common practice to the skilled person.

Thus in one embodiment the present conjugate is a fusion protein of a peptide according to the present invention, e.g. a peptide of SEQ ID NO: 1-100, with a therapeutically active protein, e.g. antibody, or a diagnostic (e.g. fluorescent) protein or both, optionally also comprising a NLS. Such a fusion protein can be prepared by expression of the appropriate DNA construct.

The present invention thus provides peptides or peptidomimetics for targeting biologically active moieties such as oligonucleotides, genes, proteins, pharmaceuticals and the like to various normal organs or tissues, especially muscle cells and the heart. Thus the invention also concerns the use of a conjugate according to the invention for the preparation of a medicament for targeting a biological active moiety or a diagnostic moiety to a muscle cell. In one embodiment the medicament is for the treatment of a muscle-cell associated disorder including cardiac disorders. Muscle-cell associated disorders include myopathies, muscular dystrophy and muscle wasting diseases. In one embodiment the medicament is for the treatment of disorders associated with myostatin. Myostatin has also been associated with diabetes mellitus type II and obesity. Thus in one embodiment the medicament is for the treatment of diabetes mellitus type II and/or obesity. In another embodiment the medicament is for the treatment of a muscle-cell associated disorder including cardiac disorders selected from the group consisting of Duchenne muscular dystrophy, Becker's muscular dystrophy, Emery-Dreifuss muscular dystrophy, Limb-girdle muscular dystrophy, Facioscapulohumeral muscular dystrophy, Myotonic dystrophy, Oculopharyngeal muscular dystrophy Congenital muscular dystrophy, Distal muscular dystrophy, Amyotrophic lateral sclerosis, Infantile spinal muscular atrophy, (Juvenile-, Intermediate- and Adult-) spinal muscular atrophy, Spinal bulbar muscular atrophy, Dermatomyositis, Polymyositis, Inclusion body myositis, Myasthenia gravis, Lambert-Eaton myasthenic syndrome, Congenital myasthenic syndrome, Hyperthyroid myopathy, Hypothyroid myopathy, Charcot-Marie-Tooth disease, Friedreich's ataxia, Dejerine-Sottas disease, Myotonia congenita (both Thomsen's and Becker's Disease), Paramyotonia congenita, Central core disease, Nemaline myopathy, Myotubular myopathy (Centronuclear myopathy), Periodic paralysis (both Hypokalemic and Hyperkalemic), Mitochondrial myopathy and muscle diseases due to deficiencies in carnitine and the following enzymes Phosphorylase, Acid Maltase (Pompe's disease), Phosphofructokinase, Debrancher enzyme (also known as Amylo-1,6-glucosidase); a glycogen storage disease also known as Forbes disease, Carnitine palmityl transferase, Phosphoglycerate kinase, Phosphoglycerate mutase, Lactate dehydrogenase and Myoadenylate deaminase.

In one embodiment the present conjugates can also be used as a tool for non-viral gene delivery or non-viral gene therapy. As a conjugate, the present peptides or petidomimetics can target gene constructs to cells, in particular muscle cells. In one embodiment the gene construct allows for the production of an enzyme in an enzyme replacement therapy or the gene construct allows for the production of a therapeutical protein such as for example Factor VIII, Factor IX, Factor VII, bilirubin UDP glucuronosyltransferase, all lysosomal storage disorder proteins such as alpha-glucosidase or in particular Aldurazyme®, Cerezyme®, Fabrazyme® or Myozyme®.

One embodiment of the invention is the targeting of a virus or viral particle to cells. In a conjugate according to the invention the virus or viral particle is the biologically active moiety. In one embodiment the peptide or peptidomimetic according to the invention is linked to the viral biologically active moiety by including the DNA/RNA sequence of the peptide or peptidomimetic in the genome of a virus such that the peptide or peptidomimetic is expressed at the outer surface of the virus or viral particle. The recombinant methodology to bring such expression about is well known to the skilled person. The peptide or peptidomimetic thus targets the virus or viral particle to specific cells/tissue. This is of particular interest for targeted vaccination, gene therapy, gene replacement or viral exon skipping constructs (AAV vectors expressing antisense sequences fused to either U1 or U7 small nuclear RNA; Denti et al., 2006, Hum. Gene Ther. 17, 565-574).

In one embodiment the peptide or peptidomimetic according to the invention is selected from the group consisting of YQDSAKT, VTYKTAS, EPLQLKM', WSLQASH, TLWVPSR, QGMHRGT, LYQDYSL' SESMSIK, LPWKPLG' QSPHTAP, TPAHPNY, SLLGSTP, TALPPSY, VNSATHS, LPLTPLP, NQLPLHA, GNTPSRA'TQTPLKQ, AMISAIH, NLTRLHT, HVIANAG, HAIYPRH and LGAQSNF (SEQ ID NOs: 7, 80-94, 17, 95, 97-99, 96, and 100, respectively).

In yet another embodiment the peptide or peptidomimetic according to the invention is selected from the group consisting of SPNSIGT, STFTHPR, QLFTSAS, STIHGST, SAPRPLY, AAQTSTP, YQDSAKT, EPLQLKM, TLWVPSR, LYQDYSL, LPWKPLG, TPAHPNY, TALPPSY, LPLTPLP, HAIYPRH and GNTPSRA (SEQ ID NOs: 1-7, 81, 83, 87, 91, 93, 96, and 17, respectively.

In yet another embodiment the peptide or peptidomimetic according to the invention is selected from the group consisting of YQDSAKT, EPLQLKM, TLWVPSR, LYQDYSL, LPWKPLG, TPAHPNY, TALPPSY, LPLTPLP, HAIYPRH and GNTPSRA (SEQ ID NOs: 7, 81, 83, 85, 87, 89, 91, 93, 96, and 17, respectively).

In one embodiment the peptide or peptidomimetic according to the invention is selected from the group consisting of YQDSAKT and GNTPSRA (SEQ ID NOs: 7 and 17).

In one embodiment the peptide or peptidomimetic according to the invention is selected from the group consisting of QLFTSAS, LYQDYSL and LGAQSNF (SEQ ID NOs: 3, 85, and 100, respectively).

Also encompassed by the present invention is DNA consisting of or comprising a sequence encoding a peptide according to the present invention and the complementary DNA sequence thereof and the RNA transcript of a DNA sequence consisting of or comprising a sequence encoding a peptide according to the present invention and the complementary RNA sequence thereof.

The present invention also relates to pharmaceutical compositions comprising a conjugate according to the invention and a pharmaceutically acceptable carrier.

EXAMPLES

Example 1

In Vitro Selection of Peptides Against Myoblasts and Myotubes

A pre-made phage peptide library containing 2 billion phages expressing random 7-mer peptides (New England Biolabs Inc.) has been screened to identify muscle-specific peptides. Briefly, the library of phage-displayed peptides was incubated with cells plated in culture flasks. After washing away the unbound phage, specifically-bound or internalized phage was eluted and amplified. After a series of different in vitro biopanning steps, including both positive and negative selection rounds on human or mouse myotubes and fibroblasts respectively, the pool was enriched for binding sequences which could be characterized by DNA sequencing. Therefore, muscle-specific peptides were identified which will bind to and be internalized by the target cells. Specific peptide sequences that were found are shown in Table 1.

TABLE 1

Peptide sequences found after in vitro selection on human and mouse myotubes

| | | | | |
|---|---|---|---|---|
| SPNSIGT[1] | STFTHPR[1] | QLFTSAS[1] | STIHGST[1] | SAPRPLY[1] |
| AAQTSTP[1] | YQDSAKT[1] | AVTINEP | VTAATLS | TYPAALL |
| ELSPSAP | TVPQLTT | QNAPPSL | YDIDNRR | QTLLPSH |
| TSFQPHR | GNTPSRA | LTQMSIS | RLTLPMP | GTAPPVH |
| HSPSKIP | FPHYPMS | ASHLEPS | AMTTKID | ATLTHPP |
| HMATFHY | LLATPTP | AQPNKFK | MPALLRS | LPPEHPL |
| AHPQLAT | YAGPYQH | HWEMWSY | QAPRLWS | HTPNSTH |
| SNQLVEG | FSPSTPN | ASSPVHR | SPHSASL | DQLPLIP |
| SLAAYLH | WSQMHFL | SIPLLNH | NQQFYIL | FESRLTA |
| QPLSNAS | KPAYGST | ANYSVSI | YSHTAAT | QHPPWRV |
| MPAVPHS | SALLPSF | THPPTTH | SNSIRPN | ASVQQRG |
| FPPSFTA | MQQGPRP | QKTALPL | TYGTKIS | SLKLLNQ |
| TSSTMNR | YKHTPTT | GSWYQVP | YYFPPFY | AYKPVGR |
| ASTLKWA | TWTFRIP | SYMIQLS | IQSPHFF | SVSPWGI |
| THLPWQT | AHSMGTG | FMSPLWT | IVNTAPL | STFTKSP |
| IPTLPSS | AFVSRQP | SSLPLRK | TYSTLGY | |

(SEQ ID NOs: 1-79)
[1]sequence found more than once

Two of the peptides that occurred frequently after selection on both mouse and human myotubes, SPNSIGT and QLFT-SAS (SEQ ID NOs: 1 and 3), were synthesized with a fluorescent label (FAM) and tested for uptake into human and mouse differentiated muscle cells (myotubes). Myotubes were obtained from confluent human KM109 myoblast cultures by 7-14 days of serum deprivation. The culture was subsequently incubated with FAM-labeled peptide and photographed with an inverted fluorescence microscope, without previous fixation. A significant uptake of these peptides into cultured myotubes was observed.

Peptide QLFTSAS (SEQ ID NO: 3), was synthesized with a fluorescent label (FAM) and subsequently conjugated to a 21-mer 2'O-methyl phosphorothioate anti-sense oligonucleotide (AON). Myotubes were obtained from confluent human KM109 myoblast cultures by 7-14 days of serum deprivation. The culture was subsequently incubated with the FAM-labeled conjugate and photographed with an inverted fluorescence microscope, without previous fixation. The photographs showed that the conjugate is taken up in cultured human differentiated muscle cells (myotubes).

Example 2

Selection of Peptides in mdx Mice

For panning experiments in mdx mice, the library was injected through the tail vein. After 10 to 20 minutes, the mice were sacrificed and perfused, after which the heart and different muscle groups were isolated. Bound and/or internalized phage was recovered from tissue homogenates, amplified, and re-applied to mdx mice. Enriched sequences were selected and further characterized. Specific peptide sequences that were found are shown in Table 2.

TABLE 2

Peptide sequences found after four rounds of in vivo selection in mdx mice, on skeletal muscle and heart

| | | | | |
|---|---|---|---|---|
| YQDSAKT[1,2] | VTYKTAS | EPLQLKM[1] | WSLQASH | TLWVPSR[1] |
| QGMHRGT | LYQDYSL[1] | SESMSIK | LPWKPLG[1] | QSPHTAP |
| TPAHPNY[1] | SLLGSTP | TALPPSY[1] | VNSATHS | LPLTPLP[1] |
| NQLPLHA | GNTPSRA[1,2] | TQTPLKQ | AMISAIH | NLTRLHT |
| HVIANAG | LGAQSNF | HAIYPRH[1] | | |

(SEQ ID NOs: 7, 80-94, 17, 95-100, and 96, respectively).
[1]sequence found more than once
[2]sequence also found after in vitro screening (see Table 1)

Three of the peptides that were found after four rounds of in vivo selection, were synthesized with a fluorescent label (FAM) and tested in cell culture for uptake on human myotubes as described in Example 1. The photographs showed that all three peptides were taken up by cultured human myotubes.

Example 3

In Vivo Staining of Muscle Fibers after Intramuscular Injection

Peptides that showed uptake into cultured human myoblasts and myotubes were synthesized with a fluorescent label (FAM) and injected into the gastrocnemius (calf muscle) of four week old mdx mice. FAM-labeled peptides QLFTSAS (SEQ ID NO: 3; 5 nmol injected), LYQDYSL (SEQ ID NO: 85; 2.5 nmol injected) and LGAQSNF (SEQ ID NO: 100; 2.5 nmol injected) were analysed. After three days the mice were sacrificed and the muscles were snap frozen. Cross-sections were cut, fixed with acetone and mounted for analysis with a fluorescence microscope. Cross-sections were cut and photographed with a fluorescence microscope (CCD camera).

The photographs showed that the peptides QLFTSAS, LYQDYSL and LGAQSNF (SEQ ID NOs: 3, 85, and 100, respectively) were taken up into a large area of muscle fibers and were still visible after 3 days. It was clearly shown that whole fibers are stained homogeneously, and that sometimes a more intense membrane staining is observed.

Uptake of the FAM-labeled peptides QLFTSAS and LGAQSNF (SEQ ID NOs: 3 and 85) was also tested on the muscle of a healthy mouse. Of each peptide 5 nmol was injected into the gastrocnemius muscle. After 3 days the mice were sacrificed and the amount of staining was assessed. Samples were photographed with an inverted fluorescence microscope. Although the muscle cells of these mice do not have compromised membranes like the muscle cells of mdx mice, still a significant area of uptake of the peptides QLFTSAS and LGAQSNF (SEQ ID NOs: 3 and 85) into the myofibers of the injected muscle was observed, as was shown on the photographs.

Example 4

Exon Skipping In Vivo by Peptide-AON Conjugates

Peptides QLFTSAS and LGAQSNF (SEQ ID NOs: 3 and 85) were conjugated to the 20-mer 2'O-methyl phosphorothioate antisense oligonucleotide (AON) M23. This AON has been shown to be able to induce skipping of exon 23, both in cell culture and in the mdx mouse model (Lu et al., 2003, Nature Med. 9, 1009-1014). The conjugates were injected into the gastrocnemius muscle of mdx mice. The mice received two injections, with a 24-h interval, of 2.9 nmol of conjugate and were sacrificed after 10 days. Subsequently, RT-PCR analysis of dystrophin mRNA was performed in the muscle.

In table 3 the skip percentages in the muscle are shown for AON M23 conjugated to peptides QLFTSAS and LGAQSNF (SEQ ID NOs: 3 and 85). Both conjugates were able to induce skipping of exon 23 in the muscle of the mdx mice within the same range as the oligonucleotide alone.

TABLE 3

Exon skipping in mdx mice by peptide-AON conjugates after intramuscular injection mdx mice

| AON-(conjugate) | skip percentage |
| --- | --- |
| naked AON | 10% |
| QLFTSAS-AON | 7.5% |
| LGAQSNF-AON | 9.5% |

With both peptide-AON conjugates the same experiment was performed in healthy mice. The muscles of these mice do not have compromised membranes like the muscles of mdx mice. As shown in table 4, also in these healthy mice both conjugates were able to induce skipping of exon 23 in the muscle.

TABLE 4

Exon skipping in healthy mice by peptide-AON conjugates after intramuscular injection healthy mice

| AON-(conjugate) | skip percentage |
| --- | --- |
| naked AON | 3% |
| QLFTSAS-AON | 3% |
| LGAQSNF-AON | 2% |

Example 5

Uptake In Vivo of Peptide-AON Conjugates

AON M23 alone and AON M23 conjugated to peptides QLFTSAS and LGAQSNF (SEQ ID NOs: 3 and 85) was injected intravenously into mdx mice. The mice received 3 injections, with a 48-h interval, of 50 mg/kg of AON alone or of the conjugate and were sacrificed after 10 days. Subsequently, the level of AON M23 in the quadriceps muscle and in the heart muscle was measured with a hybridization-ligation ELISA specific for AON M23.

In table 5 the uptake of the AON M23-peptide conjugates into quadriceps and heart muscle is shown as a percentage of the uptake of AON M23 alone (AON M23 alone uptake is set at 100%). It is shown that uptake of the conjugates into quadriceps muscle is more than twice as high and into the heart muscle more than three times as high as with M23 AON alone.

TABLE 5

Uptake of peptide-AON conjugates into quadriceps and heart muscle after systemic delivery, relative to uptake of naked AON (set at 100%)

| | quadriceps | heart |
| --- | --- | --- |
| naked AON | 100% | 100% |
| QLFTSAS-AON | 201% | 333% |
| LGAQSNF-AON | 231% | 331% |

Example 6

In Vivo Targeting after Systemic Delivery

Peptide LGAQSNF (SEQ ID NO: 85) was synthesized with the fluorescent label Cy5. This label can be detected with a high sensitivity by a fluorescence imaging system (NightOWL, Berthold Technologies) after systemic (intravenous or subcutaneous) injection into a mouse. This enables monitoring of the distribution across the different organs of a living mouse after injection of the compound. Of this peptide, 71 nmol was injected subcutaneously on the back of an mdx mouse and after 48 hours a picture was taken with the imaging system.

The figure shows the distribution of the Cy5-labeled peptide LGAQSNF (SEQ ID NO: 85) 48 hours after subcutaneous injection in an mdx mouse. The mouse is lying on its back, and the back paws and an area on the abdomen were first shaved because the hairs on the skin impair detection of the signal. A clear signal could be detected in the back and front paws and in the tail. The signal in the shaved area on the abdomen is likely from abdominal muscle. This result indicates that the peptide, which was injected on the back, is taken up by the abdominal muscle and by muscles in the hindlegs, paws and tail of the mouse.

Example 7

Targeting of Proteins into Muscle Cells

To examine the ability of the peptides LGAQSNF and QLFTSAS (SEQ ID NOs: 3 and 85) to transport a protein into muscle cells, DNA constructs were prepared in which the peptide sequence was fused to the protein sequence. The following constructs were prepared and expressed using a bacterial expression vector:

LGAQSNF-NLS-3F5-GFP
LGAQSNF-3F5-GFP
QLFTSAS-NLS-3F5-GFP
QLFTSAS-3F5-GFP
NLS: nuclear localization sequence KKRK
VHH 3F5: llama derived antibody
GFP: green fluorescence protein Immortomouse IM2 myoblasts were incubated with purified LGAQSNF-NLS-3F5-GFP protein overnight. The next day, fluorescence imaging was performed to assess uptake of the protein construct into the cells. The pictures showed that the protein was taken up into the cytoplasm of the cells. This indicates that the targeting peptides are able to transport a large protein into muscle cells.

The invention claimed is:

1. A conjugate of a peptide or peptidomimetic comprising the sequence or consisting of the sequence NLTRLHT (SEQ ID NO: 98) linked to a moiety selected from a biologically active moiety and diagnostic moiety.

2. The conjugate according to claim 1, wherein the biologically active moiety is selected from the group consisting of DNA, RNA or analogues thereof.

3. The conjugate according to claim 2, wherein the biologically active moiety is a DNA, RNA or analogues thereof selected from the group consisting of: 2'-O-alkyl, 2'-O-methoxyethyl-, 2'-O-methyl, 2'-O-alkenyl (allyl), 2'-O-alkynyl nucleotides, locked nucleic acids (LNAs), peptide nucleic acids (PNAs), ethylene bridged nucleic acids (ENAs), phosphorothioate modified nucleotides, morpholino based nucleotides and combinations thereof.

4. The conjugate according to claim 1, wherein the conjugate is a fusion protein comprising a peptide of SEQ ID NO: 98 and a therapeutically active protein and/or a diagnostic protein.

5. The conjugate according to claim 4, which further comprises a nuclear localisation signal.

6. A pharmaceutical composition comprising a conjugate according to claim 1 in combination with a pharmaceutically acceptable carrier.

7. The pharmaceutical composition according to claim 6, wherein the pharmaceutical composition is for the treatment of a muscle-cell associated disorder including cardiac disorders.

8. The pharmaceutical composition according to claim 7, wherein the pharmaceutical composition is for the treatment of a myopathy, muscular dystrophy or muscle wasting disease.

9. The pharmaceutical composition according to claim 6, wherein the pharmaceutical composition is for the treatment of diabetes mellitus type II or obesity.

10. A molecule comprising a peptide or peptidomimetic comprising the sequence or consisting of the sequence NLTRLHT (SEQ ID NO: 98) and a linking portion which is not a peptide for linking the molecule to a biologically active moiety or a diagnostic moiety.

* * * * *